US00PP30259P2

(12) United States Plant Patent
Meilland

(10) Patent No.: US PP30,259 P2
(45) Date of Patent: Mar. 5, 2019

(54) CREEPING ROSE PLANT NAMED 'MEILOWMYE'

(50) Latin Name: *Rosa hybrida*
Varietal Denomination: Meilowmye

(71) Applicant: The Conard-Pyle Company, West Grove, PA (US)

(72) Inventor: Alain Antoine Meilland, Antibes (FR)

(73) Assignee: The Conard-Pyle Company, West Grove, PA (US)

( * ) Notice: Subject to any disclaimer, the term of this patent is extended or adjusted under 35 U.S.C. 154(b) by 0 days.

(21) Appl. No.: 15/731,761

(22) Filed: Jul. 31, 2017

(51) Int. Cl.
*A01H 5/02* (2018.01)

(52) U.S. Cl.
USPC ..... Plt./104

(58) Field of Classification Search
USPC ..... Plt./145, 141, 134, 104, 111, 102
CPC ..... A01H 5/0222; A01H 5/02; A01H 5/00; A01H 6/749
See application file for complete search history.

(56) References Cited

U.S. PATENT DOCUMENTS

PP15,960 P3 9/2005 Meilland
PP19,143 P2 8/2008 Meilland

OTHER PUBLICATIONS

World Federation of Rose Societies Rose Trials 2010, retrieved on Jul. 9, 2018, retrieved from the Internet at www.worldrose.org/trials/2010/monza/monza6.asp, one page. (Year: 2010).*

* cited by examiner

*Primary Examiner* — June Hwu
(74) *Attorney, Agent, or Firm* — Buchanan Ingersoll & Rooney PC

(57) ABSTRACT

A new and distinct variety of Creeping rose plant, herein referred to by its cultivar name, 'Meilowmye', is provided which forms in abundance on a nearly continuous basis attractive, cup-shaped, flowers that are yellow colored in the course of opening and salmon colored when completely open. Attractive, semi-glossy foliage is formed and the plant is healthy, compact, and low. The tolerance to disease is good, particularly with respect to black spot. The new variety is well suited for providing attractive ornamentation in the landscape.

1 Drawing Sheet

Figures 1, 2, 3, 4, 5, 6, 7, 8, 9, 10, 11, 12, 13, 14, 15, 16, 17, 18:
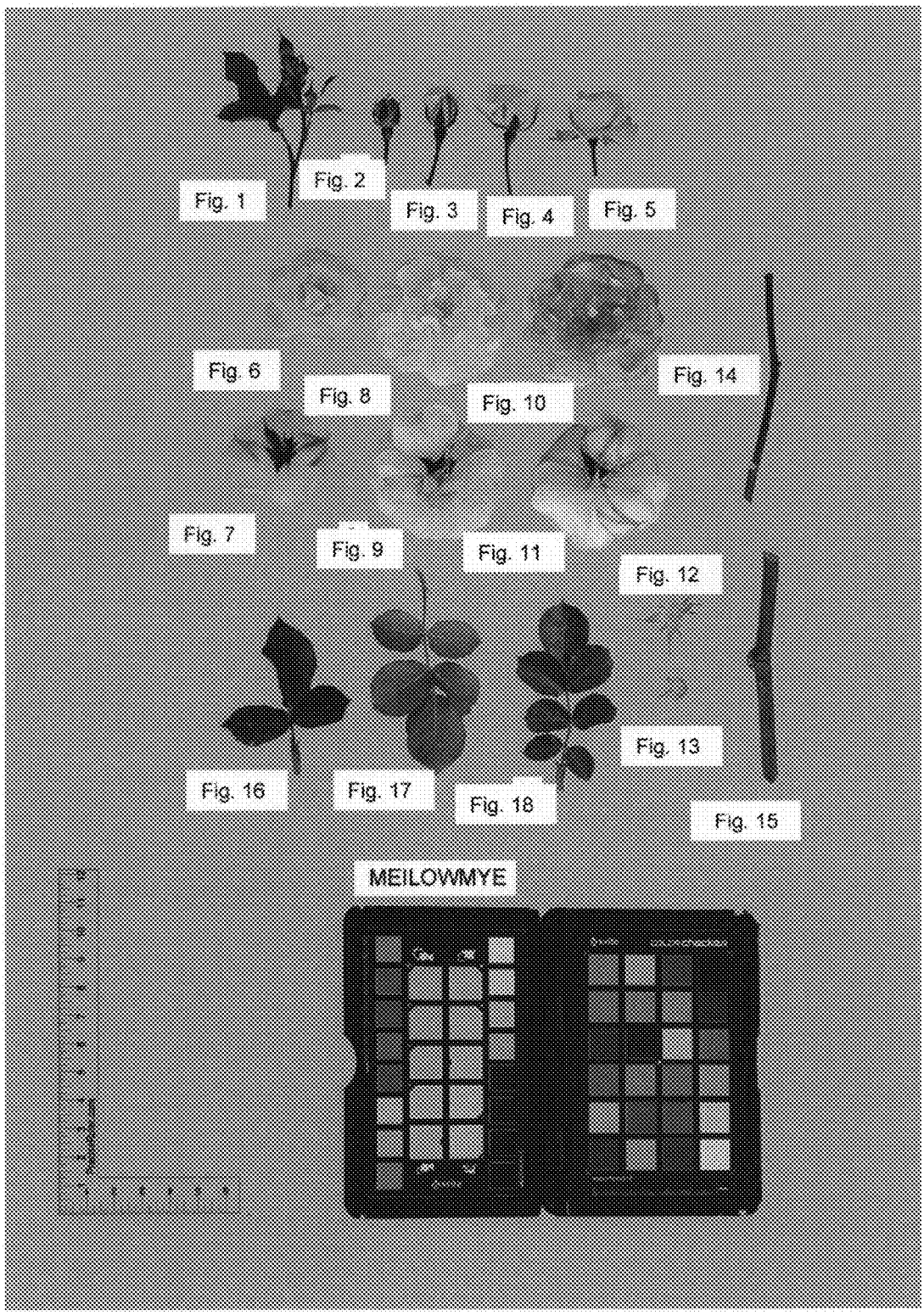

Botanical/commercial classification:
Latin name—*Rosa hybrida.*
Common name—Creeping Rose Plant.
Varietal denomination—'Meilowmye'.

SUMMARY OF THE INVENTION

The new variety of *Rosa hybrida* Creeping rose plant of the present invention was created by artificial pollination wherein two parents were crossed which previously had been studied in the hope that they would contribute the desired characteristics. The female parent (i.e., seed parent) of the new variety was the product of the cross of the 'Meijeunom' variety (U.S. Plant Pat. No. 19,143) and the 'Meiglise' variety (U.S. Plant Pat. No. 15,960). The male parent (i.e., pollen parent) was the 'Meibalneo' variety (non-patented in the United States).

The parentage can be summarized as follows:

('Meijeunom' x 'Meiglise') x 'Meibalneo'.

The seeds resulting from the above pollination were sown and small plants were obtained which were physically and biologically different from each other. Selective study resulted in the identification of a single plant of the new variety.

It was found that the new Creeping rose plant of the present invention possesses the following combination of characteristics:

(a) displays a healthy, compact, and low plant,
(b) exhibits a yellow coloration of the flower in the course of opening to a salmon coloration once completely open,
(c) blooming is early in the season and is very abundant and nearly continuous,
(d) shows a good tolerance to disease, particularly with respect to black spot, and
(e) is well suited for providing attractive ornamentation.

The new variety well meets the needs of the horticultural industry. It can be grown to advantage as ornamentation in parks, gardens, public areas, and in residential settings. Accordingly, the plant is particularly well suited for growing in the landscape.

The new variety can be readily distinguished from its ancestors. More specifically, while the new variety has flowers that are yellow to salmon in coloration, the 'Meijeunom' variety displays ivory-white colored flowers, the 'Meiglise' variety displays white flowers, and the ('Meijeunome' x 'Meiglise') variety (i.e., the seed parent) displays white flowers. Further, the 'Meibalneo' variety (i.e., the pollen parent) typically has more than 90 petals per flower, while the new variety has 32 petals per flower, on average.

The new variety has been found to undergo asexual propagation in Le Cannet des Maures, Var, France by a number of routes, including budding, grafting, and the rooting of cuttings. Asexual propagation by the above-mentioned techniques in France has shown that the characteristics of the new variety are stable and strictly transmissible by such asexual propagation from one generation to another. Accordingly, the new variety undergoes asexual propagation in a true-to-type manner.

The new variety has been named 'Meilowmye'.

BRIEF DESCRIPTION OF THE PHOTOGRAPHS

The accompanying photographs show, as nearly true as it is reasonably possible to make the same in color illustrations of this character, typical specimens of the new variety. The illustrated rose plants of the new variety were approximately two years of age and were observed during July while budded on their own roots and growing outdoors at Le Cannet des Maures, Var, France. Dimensions in centimeters are indicated at the bottom of the photograph. Standard color information is included at the bottom of the photograph.

FIG. 1—illustrates a specimen of a young shoot.

FIG. 2—illustrates a specimen of a floral bud before the opening of the sepals.

FIG. 3—illustrates a specimen of a floral bud at the opening of the sepals.

FIG. 4—illustrates a specimen of a floral bud at the opening to the petals.

FIG. 5—illustrates a specimen of a flower in the course of opening.

FIG. 6—illustrates a specimen of a flower in the course of opening—plan view—obverse.

FIG. 7—illustrates a specimen of a flower in the course of opening—plan view—reverse.

FIG. 8—illustrates a specimen of a flower in the course of opening—plan view—obverse.

FIG. 9—illustrates a specimen of a flower in the course of opening—plan view—reverse.

FIG. 10—illustrates a specimen of a fully open flower—plan view—obverse.

FIG. 11—illustrates a specimen of a fully open flower—plan view—reverse.

FIG. 12—illustrates a specimen of a floral receptacle showing arrangement of the stamens and pistils.

FIG. 13—illustrates a specimen of a floral receptacle showing arrangement of the pistils (stamens removed).

FIG. 14—illustrates a specimen of a flowering stem.

FIG. 15—illustrates a specimen of a main branch.

FIG. 16—illustrates a specimen of a leaf with 3 leaflets—plan view—upper surface.

FIG. 17—illustrates a specimen of a leaf with 5 leaflets—plan view—under surface.

FIG. 18—illustrates a specimen of a leaf with 7 leaflets—plan view—upper surface.

DETAILED BOTANICAL DESCRIPTION

The chart used in the identification of colors is that of The Royal Horticultural Society (R.H.S. Colour Chart, 2001 Edition), London, England. The terminology which precedes reference to the chart has been added to indicate the corresponding color in more common terms. The description is based on the observation of two-year-old specimens of the new variety during July while budded on their own roots and growing outdoors at Le Cannet des Maures, Var, France.

Class: Creeping.

Plant:

*Habit*.—Creeping.

*Height*.—Approximately near 30 to 50 cm on average.

*Spread*.—Approximately near 50 to 70 cm on average.

Branches:

*Color*.—Commonly near Green Group 138 A on young stems and on adult wood.

*Thorns*.—No thorns observed.

Foliage:

*General appearance*.—Very dense with a semi-glossy aspect.

*Number of leaflets*.—3, 5, and 7; most often 5 or 7.

*Terminal leaflet*.—Length: approximately 4 cm on average. Width: approximately 2.4 cm on average.

*New foliage*.—Upper surface color: commonly near Green Group 138A. Under surface color: commonly near Green Group 138B. Anthocyanin coloration: moderate intensity and commonly near Red Group 46A.

*Old foliage*.—Upper surface color: commonly near Green Group 137A. Under surface color: commonly near Green Group 138A.

Leaflets:

*Shape*.—Generally oval shaped with an acuminate tip and an obtuse base.

*Texture*.—Leathery.

*Edge*.—Slightly denticulate.

*Serration*.—Small and single.

*Undulation of margin*.—Absent to weak.

*Rachis*.—Color of upper surface: commonly near Yellow Green Group 147D. Color of under surface: commonly near Green Group 138A.

*Petioles*.—Upper surface texture: no glandular. Under surface texture: few prickles. Color of upper surface: commonly near Green Group 137A. Color of under surface: commonly near Green Group 138A. Petiole length of terminal leaflet: near 1.5 cm on average.

*Stipules*.—General appearance: adnate, pectinate, and narrow. Length: near 1.2 cm on average. Width: near 0.4 cm on average. Color of upper surface: commonly near Yellow Green Group 147C. Color of under surface: commonly near Green Group 138A.

Inflorescence:

*Number of flowers per stem*.—Commonly 5 to 15 blossoms per stem.

*Flower type*.—Panicle.

*Buds*.—Shape: conical. Size: small. Length: approximately 1 cm on average. Width: approximately 0.8 cm on average. Color as calyx breaks, upper and under surfaces: commonly near Yellow Group 13B slightly suffused with near Orange Group 24B.

*Sepals*.—Length: approximately 1.4 cm on average. Width: near 0.6 cm on average. Shape: slightly elongated at the top and upright at the base. Extension: very weak. Upper surface texture: pubescent. Upper surface color: commonly near Green Group 138C. Under surface texture: smooth. Under surface color: commonly near Green Group 138B and anthocyanin coloration near Greyed Orange Group 173A.

*Receptacle*.—Color: commonly near Green Group 138B. Length: approximately 0.5 cm on average. Width: approximately 0.3 cm on average. Surface: smooth. Shape: funnel shaped.

*Peduncle*.—Length: near 3 to 3.5 cm on average. Width: approximately 0.2 cm on average. Surface: glandular. Color: commonly near Green Group 138B and anthocyanin coloration near Greyed Orange Group 173A.

*Flower*.—Average open size: typically near 5 cm to 7 cm. Shape: cup shaped. Number of petals: commonly 32 on average. Shape of petal: cuneiform at the base and rounded at the top. Texture of the petal: flexible. Petal length: approximately 2.4 cm on average. Petal width: approximately 1.1 cm on average. Petal undulation: very weak to weak. Petal arrangement: imbricated without petaloids. Petal drop: petals drop off cleanly before drying. Basal petal spot: none observed. Fragrance: none. Color at the begin of the opening on upper surface: commonly near Yellow Group 13B slightly suffused with near Yellow Orange Group 24B. Color at the begin of the opening on the under surface: commonly near Yellow Group 13B slightly suffused with near Yellow Orange Group 24B and sometimes few petals are streaked with near Red Group 53D. Color when opening on upper surface: commonly near Yellow Group 8B. Color when opening on under surface: commonly near Yellow Group 8B and sometimes few petals are streaked with near Red Group 53D, which depends on exposure. Color of the open flower on upper surface: commonly near Yellow White Group 158D more or less suffused and margined with near Red Group 36B to Red Group 36C. Color of open flower on under surface: commonly near Yellow White Group 158D suffused and margined with Red Group 36B to Red Group 36C, and sometimes few petals are streaked with near Red Group 53D, which depends on exposure. Fading: no change in color designation of the opened flower when fading. Anthers: number is approximately 60 on average, length is approximately 0.1 cm on average, coloration is commonly near Orange Group 24C, and arrangement is regular around styles. Filaments: length is approximately 0.2 cm on average, and coloration is commonly near Yellow Group 2D. Styles: number is approximately 35 on average, length is approximately 0.3 cm on average, and coloration is commonly near Yellow Green Group 150D. Stigmas: size is approximately 0.1 cm on average and coloration is commonly near Yellow Green Group 150D. Seeds: approximately 1 to 3 seeds per fruit, shape is oblong, color is commonly near Greyed Orange Group 163C, diameter is approximately 0.3 to 0.4 cm on average, and length is approximately 0.3 to 0.5 cm on average. Pollen: not available at this stage.

Development:

*Vegetation*.—Strong.

*Hardiness zone*.—Zone 5.

*Blooming*.—Early in the season, very abundant and nearly continuous from early in May to October.

*Lastingness of individual flower*.—Commonly 6 to 10 days.

*Tolerance to diseases*.—Good, and particularly against black spot (*Diplocarpon rosae*).

Plants of the 'Meilowmye' variety have not been observed under all possible environmental conditions to date. Accordingly, it is possible that the phenotypic expression may vary somewhat with changes in light intensity and duration, cultural practices, and other environmental conditions.

I claim:

1. A new and distinct Creeping rose plant characterized by the following combination of characteristics:

(a) displays a healthy, compact, and low plant, (b) exhibits a yellow coloration of the flower in the course of opening to a salmon coloration once completely open, (c) blooming is early in the season and is very abundant and nearly continuous, (d) shows a good tolerance to disease, particularly with respect to black spot, and (e) is well suited for providing attractive ornamentation; substantially as herein shown and described.

* * * * *

MEILOWMYE